US011027107B2

(12) United States Patent
Garcia et al.

(10) Patent No.: US 11,027,107 B2
(45) Date of Patent: Jun. 8, 2021

(54) SUBCUTANEOUS VASCULAR ACCESS ASSEMBLIES AND RELATED DEVICES AND METHODS

(71) Applicant: Merit Medical Systems, Inc., South Jordan, UT (US)

(72) Inventors: Mark Garcia, Wilmington, DE (US); John Hall, North Salt Lake, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 652 days.

(21) Appl. No.: 15/783,004

(22) Filed: Oct. 13, 2017

(65) Prior Publication Data

US 2018/0104464 A1 Apr. 19, 2018

Related U.S. Application Data

(60) Provisional application No. 62/410,047, filed on Oct. 19, 2016.

(51) Int. Cl.
*A61M 39/02* (2006.01)
*A61B 17/34* (2006.01)
(Continued)

(52) U.S. Cl.
CPC ..... *A61M 39/0208* (2013.01); *A61B 17/3468* (2013.01); *A61F 2/07* (2013.01);
(Continued)

(58) Field of Classification Search
CPC .. A61M 39/0208; A61M 39/04; A61M 39/06; A61M 1/14; A61M 1/3655; A61M 25/0194; A61F 2/07; A61F 2/856; A61F 2/954; A61F 2002/061; A61F 2002/065; A61B 17/11; A61B 17/3468
See application file for complete search history.

(56) References Cited

U.S. PATENT DOCUMENTS

| 5,755,778 A | * | 5/1998 | Kleshinski | A61F 2/91 |
|---|---|---|---|---|
| | | | | 623/1.13 |
| 7,708,773 B2 | | 5/2010 | Pinchuk et al. | |

(Continued)

FOREIGN PATENT DOCUMENTS

| WO | 199819607 | 5/1998 |
|---|---|---|
| WO | 2015190928 | 12/2015 |

OTHER PUBLICATIONS

Gore Hybrid Vascular Graft, Optimal Outflow with Expanded Treatment Options Brochure, Jan. 2013.
(Continued)

*Primary Examiner* — Philip R Wiest
(74) *Attorney, Agent, or Firm* — Stoel Rives LLP

(57) ABSTRACT

Vascular access devices, assemblies, kits, and related methods are disclosed. A vascular access assembly may include a first tubular conduit, a second tubular conduit, and an expandable stent graft that is coupled adjacent to a peripheral end of the second tubular conduit. When implanted into the patient, vascular access assemblies may form a flow path that extends from an artery or an arteriovenous graft to a heart of a patient. The vascular access assembly, when implanted and assembled, may be a fully subcutaneous surgical implant.

20 Claims, 12 Drawing Sheets

(51) Int. Cl.
  *A61F 2/07* (2013.01)
  *A61M 1/14* (2006.01)
  *A61M 1/36* (2006.01)
  *A61M 25/01* (2006.01)
  *A61M 39/04* (2006.01)
  *A61M 39/06* (2006.01)
  *A61F 2/06* (2013.01)
  *A61B 17/00* (2006.01)
  *A61F 2/856* (2013.01)
  *A61F 2/954* (2013.01)

(52) U.S. Cl.
  CPC ............ *A61M 1/14* (2013.01); *A61M 1/3655* (2013.01); *A61M 25/0194* (2013.01); *A61M 39/04* (2013.01); *A61M 39/06* (2013.01); *A61B 2017/00292* (2013.01); *A61F 2/856* (2013.01); *A61F 2/954* (2013.01); *A61F 2002/061* (2013.01); *A61F 2002/065* (2013.01); *A61M 2039/0223* (2013.01); *A61M 2210/125* (2013.01)

(56) References Cited

U.S. PATENT DOCUMENTS

| | | | |
|---|---|---|---|
| 8,690,815 B2 | 4/2014 | Porter et al. | |
| 2005/0038455 A1* | 2/2005 | Bates | A61F 2/07 606/153 |
| 2006/0064159 A1* | 3/2006 | Porter | A61B 17/11 623/1.24 |
| 2010/0191322 A1 | 7/2010 | Anwar et al. | |
| 2011/0087063 A1 | 4/2011 | Farnan | |
| 2013/0035752 A1 | 2/2013 | Chang | |
| 2015/0082604 A1* | 3/2015 | Cully | A61F 2/07 29/458 |

OTHER PUBLICATIONS

Hero Graft Brochure—Reducing Catheter Dependency (No date available).
Instructions for Use—HeRO Graft (No dated available).
International Search Report and Written Opinion dated Jan. 15, 2018 for PCT/US2017/056471.
European Search Report dated May 11, 2020 for EP117862588.5.

\* cited by examiner

SUBCUTANEOUS VASCULAR ACCESS ASSEMBLIES AND RELATED DEVICES AND METHODS

RELATED APPLICATIONS

This application claims priority to U.S. Provisional Application No. 62/410,047, filed on Oct. 19, 2016 and titled, "Subcutaneous Vascular Access Assemblies and Related Devices and Methods," which is hereby incorporated by reference in its entirety.

TECHNICAL FIELD

The present disclosure relates generally to the field of medical devices. More particularly, some embodiments relate to vascular access technologies, such as vascular access assemblies that facilitate hemodialysis.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
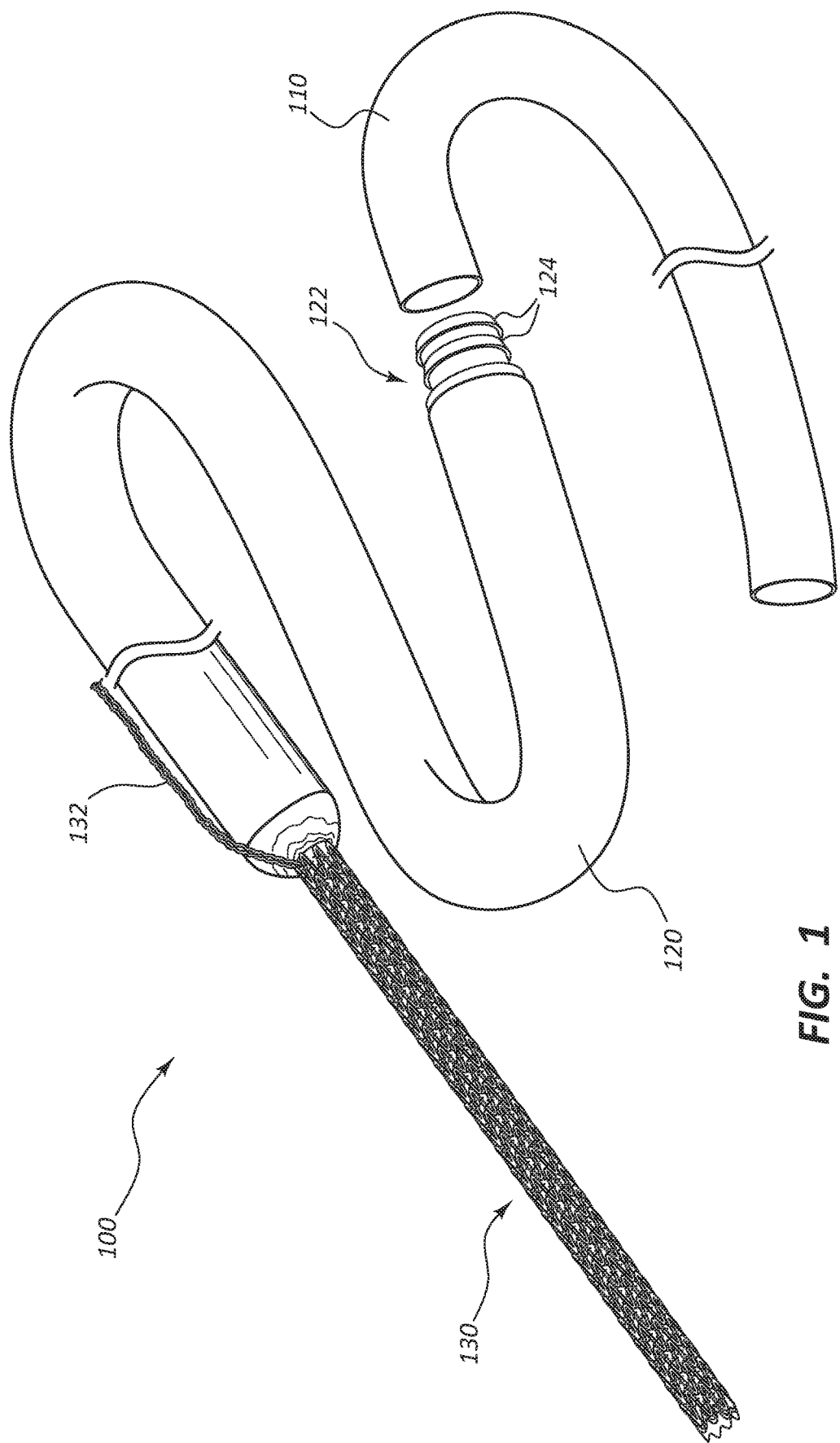
FIG. 1 is a perspective view of a vascular access assembly with an expandable stent graft in a compact state.

Many patients that suffer from kidney malfunction undergo hemodialysis to remove waste products from their blood. Hemodialysis generally requires access to an adequate blood supply. In some cases, access to a blood supply may be established via an arteriovenous fistula. In other circumstances, other methods for accessing the blood supply are used.

For example, in some embodiments, access to a blood supply is established via an arteriovenous graft. In other embodiments, access to a blood supply is established via a graft that extends from a peripheral blood supply to an outlet that is positioned in the central venous system.

Certain embodiments disclosed herein may be used to establish an artificial blood flow path, such as along a non-natural or artificial conduit, that improves or provides alternative access to a blood supply. The artificial flow path may be used, for example, to bypass a central venous stenosis. In some embodiments, the artificial blood flow path, when implanted into a patient, is fully subcutaneous. Access to a blood supply that is provided by an artificial flow path may be particularly advantageous for access in hemodialysis patients (such as hemodialysis patients that have exhausted peripheral venous access sites for fistulas).

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to each other through an intermediate component. The phrase "attached to" refers to interaction between two or more entities which are in direct contact with each other and/or are separated from each other only by a fastener of any suitable variety (e.g., an adhesive). The phrase "fluid communication" is broad enough to refer to arrangements in which a fluid (e.g., blood) can flow from one element to another element when the elements are in fluid communication with each other. Unless otherwise stated, all ranges include both endpoints and all numbers between the endpoints.

The terms "central" and "peripheral," as used herein, are opposite directional terms. For example, a peripheral end of a device or component is the end of the device or component that is furthest from the heart when the device or component is assembled and implanted within the patient. The central end refers to the opposite end, or the end closest to the heart of the patient when the device is in use. Further, this reference frame is applied herein to devices configured or designed to have one end (a central end) positioned closer to the heart when the device is in use, whether or not the device itself is deployed within the body.

Figure 2:
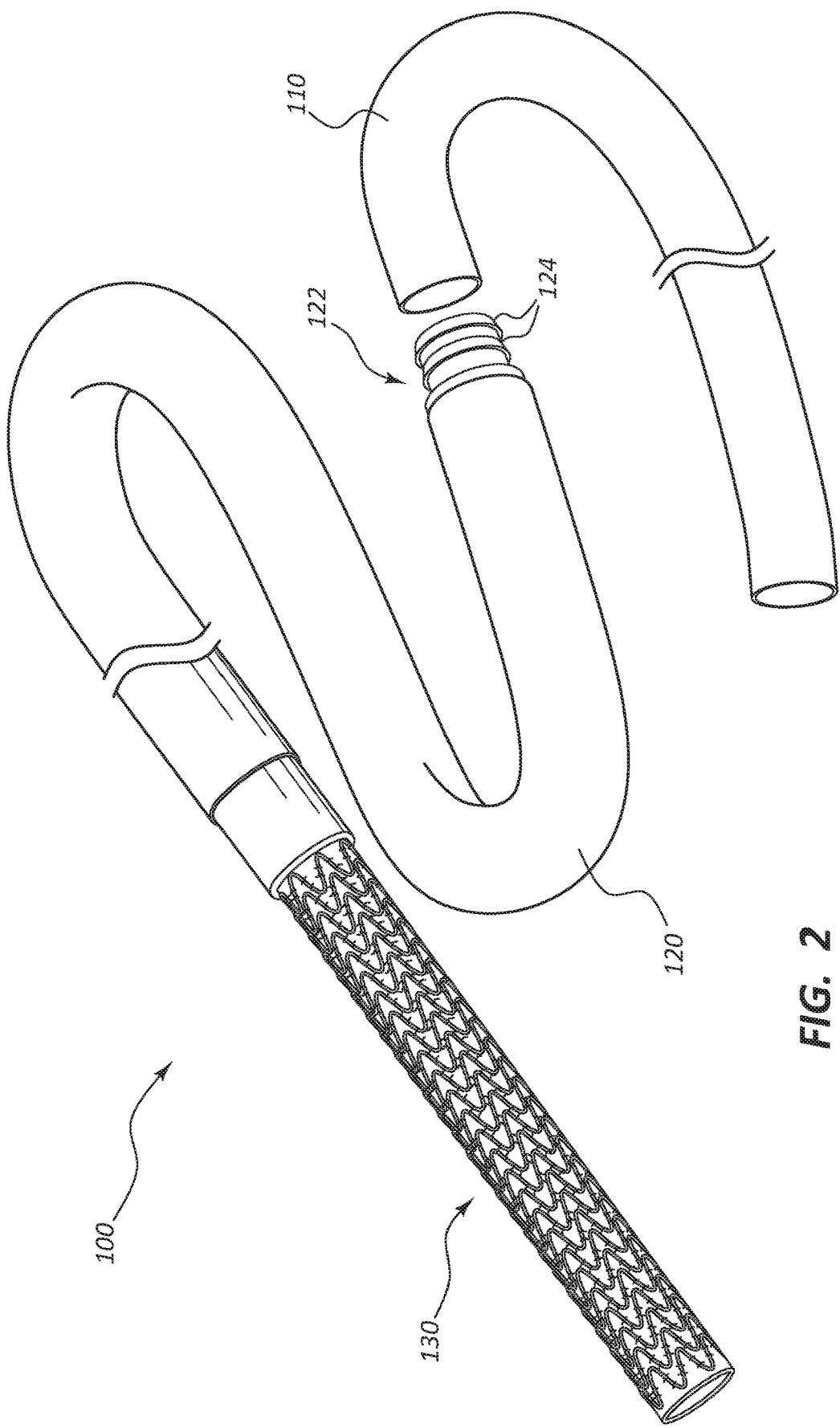
FIG. 2 is a perspective view of the vascular access assembly of FIG. 1 with the expandable stent graft in an expanded state.

FIGS. 1 and 2 provide perspective views of a vascular access assembly 100 in different states. As shown in FIGS. 1 and 2, the vascular access assembly 100 includes a first tubular conduit 110, a second tubular conduit 120, and an expandable stent graft 130.

In some embodiments, the first tubular conduit 110 has an initial length of at least 20 cm, at least 25 cm, at least 30 cm, and/or at least 35 cm. For example, the first tubular conduit 110 may have an initial length of between 20 cm and 50 cm and/or between 35 cm and 45 cm. In some embodiments, the first tubular conduit 110 has an internal diameter of between 3.5 mm and 6.5 mm. For example, in some embodiments, the internal diameter of the first tubular conduit 110 is between 4.5 mm and 5.5 mm.

In some embodiments, the first tubular conduit 110 is resistant to kinking and/or crush forces. In some embodiments, the first tubular conduit 110 is reinforced with nitinol, such as braided nitinol, which provides resistance to kinking and/or crush forces. More specifically, in some embodiments, the first tubular conduit 110 includes silicone-coated nitinol.

In some embodiments, the first tubular conduit 110 includes one or more radiopaque bands or markers (not shown). For example, the first tubular conduit 110 may include a radiopaque band adjacent the central end of the first tubular conduit 110. The radiopaque band(s) or marker(s) may facilitate fluoroscopic placement of the first tubular conduit 110 within a patient.

In some embodiments, the second tubular conduit 120 is configured to be accessed for hemodialysis. In other words, during some medical procedures (e.g., hemodialysis), the second tubular conduit 120 may be accessed in lieu of the natural vasculature of a patient. In some embodiments, the second tubular conduit 120 comprises and/or consists of polytetrafluoroethylene (PTFE), such as expanded PTFE (ePTFE), rotational spun PTFE, or electrospun PTFE. In some embodiments, the second tubular conduit 120 comprises silicone. In some embodiments, the second tubular conduit 120 comprises a fibrous polymer.

In some embodiments, the second tubular conduit 120 includes a puncturable and self-sealing wall such that the wall may be punctured by insertion of a needle and then reseal upon withdrawal of the needle. The self-sealing wall may be of any suitable composition. In some embodiments, the self-sealing wall is a multi-layered construct. For example, some embodiments include an outer layer, an inner layer, and at least one tie layer disposed between the outer layer and the inner layer. In some embodiments, one or more of the outer layer and the inner layer comprise PTFE. For example, the outer layer may comprise or consist of expanded PTFE, while the inner layer comprises and/or consists of rotational spun or electrospun PTFE. In some embodiments, the tie layer comprises an elastomer, such as elastomeric silicone. Due, at least in part, to the properties of the silicone, the resulting construct may be self-sealing. In other words, when a needle that has been inserted through the wall is withdrawn from the second tubular conduit 120, the wall may seal itself, thereby preventing leakage of blood from the second tubular conduit 120.

In some embodiments, the second tubular conduit 120 has an initial length of at least 30 cm, at least 40 cm, and/or at least 45 cm. In some embodiments, the second tubular conduit 120 is between 30 cm and 70 cm and/or between 40 cm and 60 cm in length. In some embodiments, the second tubular conduit 120 has an internal diameter of between 4.5 mm and 8 mm. For example, in some embodiments, the internal diameter of the second tubular conduit 120 is between 5.5 mm and 6.5 mm.

In some embodiments, both the first tubular conduit 110 and the second tubular conduit 120 are self-sealing. In other embodiments, only the second tubular conduit 120 is self-sealing.

The expandable stent graft 130 may be coupled to and disposed adjacent to a peripheral end of the second tubular conduit 120. In some embodiments, the expandable stent graft 130 is coupled to the peripheral end of the second tubular conduit 120 such that there is a continuous luminal surface for contacting blood. For example, in some embodiments, the vascular access assembly 100 includes a tubular liner that is disposed within both the expandable stent graft 130 and the second tubular conduit 120. The tubular liner may provide a continuous luminal surface for contact with blood from the patient. In this manner, the luminal surface formed by the expandable stent graft 130 and the second tubular conduit 120 may be free from seams, joints, or other discontinuities.

Figure 9:
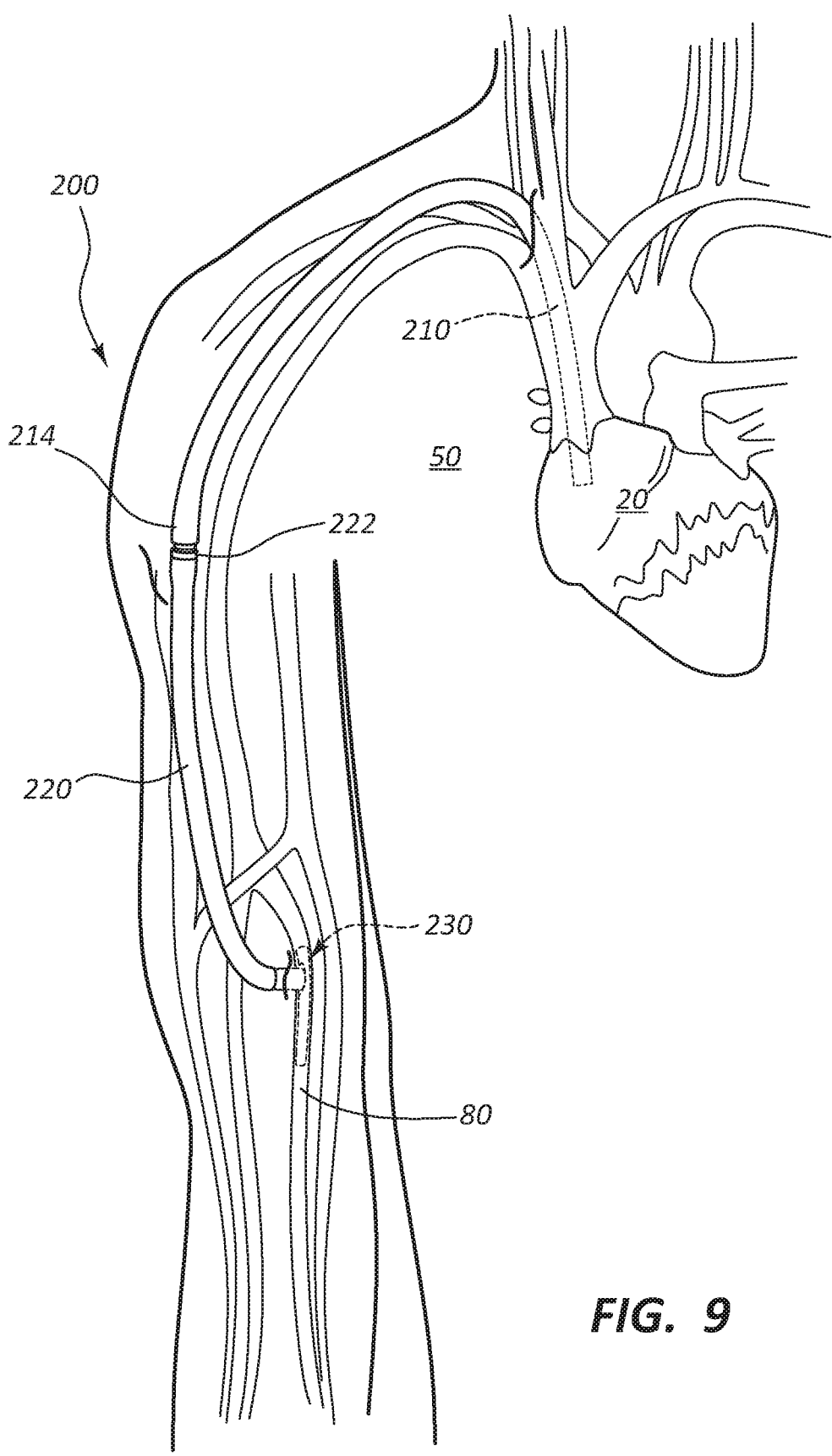
FIG. 9 depicts an implanted vascular access assembly according to another embodiment in which the second tubular conduit is coupled to a branched stent graft.
Figure 10:
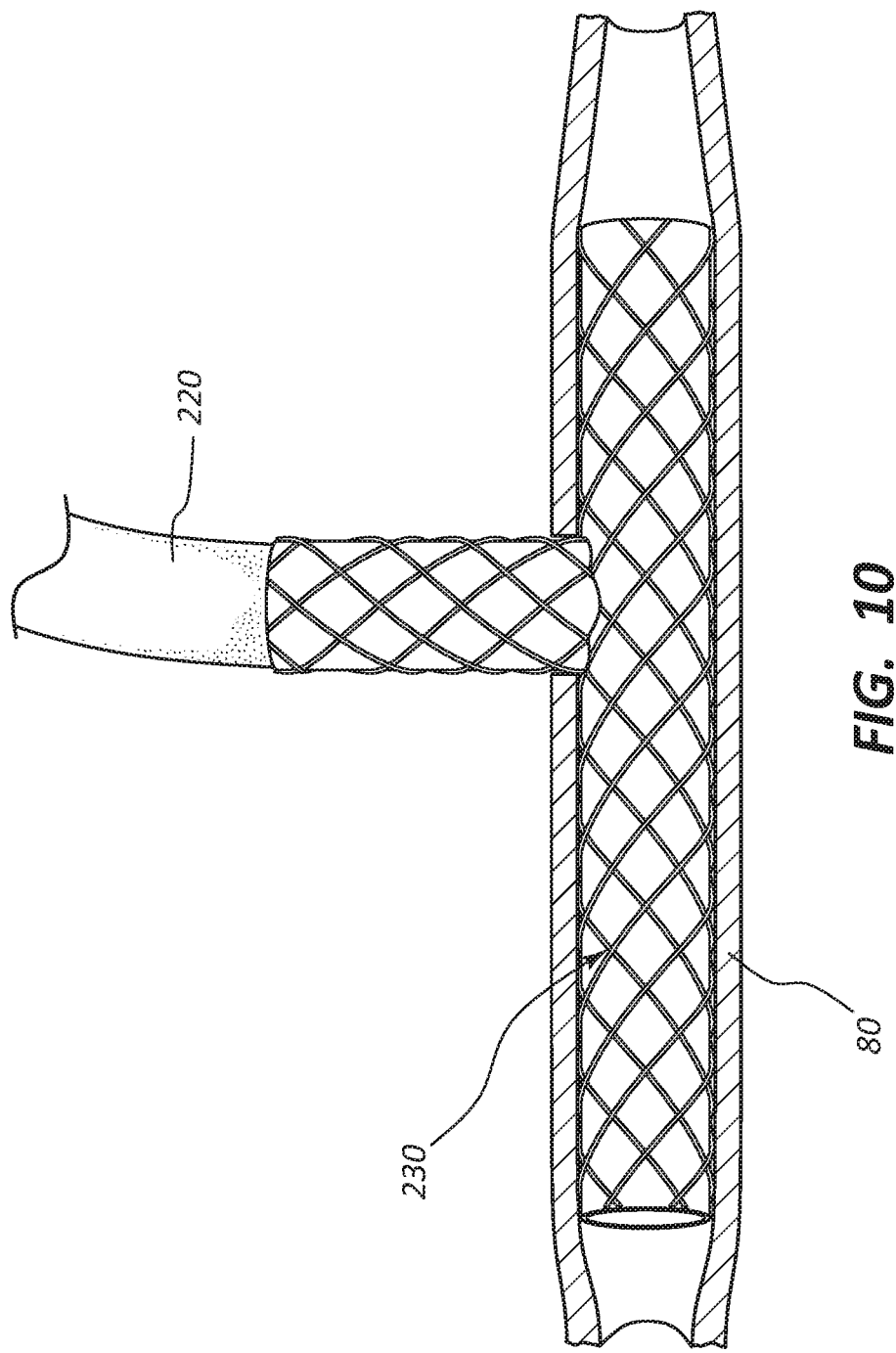
FIG. 10 depicts a portion of the implanted vascular access assembly of FIG. 9.

The expandable stent graft 130 may be unbranched as depicted in FIGS. 1-2 or branched (see FIGS. 9 and 10). The unbranched expandable stent graft 130 may be sized for positioning within and coupling to an arteriovenous graft of a patient. In other words, the unbranched expandable stent graft 130 may be positioned within a blocked or failing artervenious graft to divert substantially all of the blood from the arteriovenous graft to a flow path defined, at least in part, by the second tubular conduit 120.

The stent of the expandable stent graft 130 may be made from any suitable material, such as steel or nitinol. The expandable stent graft 130 may also include a coat. The coat may be made from any suitable material. For example, in some embodiments, the coat is formed from PTFE, such as fibrous (e.g., electrospun or rotational spun) PTFE. Other polymers may also be used to form the coat of the expandable stent graft 130. The expandable stent graft 130 may be configured to transition from a compact state as shown in FIG. 1 to a deployed state as shown in FIG. 2. In some embodiments, the expandable stent graft 130 is expanded (and thereby deployed) by inflation of a balloon that is positioned within a lumen of the expandable stent graft 130. In other embodiments, the expandable stent graft 130 is a self-expanding stent graft that transitions from the compact state to the expanded state when a restraint, such as a sheath or other delivery constraint, is removed from around the expandable stent graft 130. The restraint may be removed by any suitable manner, such as by retraction of a sheath or by use of a pull string 132 that releases the restraint. For example, a restraint may comprise filaments that extend around a circumference of the expandable stent graft 130 in a compressed state. These filaments may be coupled to the pull string 132 such that displacement of the pull string 132 decouples the filaments from the expandable stent graft 130 allowing the expandable stent graft 130 to expand. The expandable stent graft 130 may be biased to adopt the expanded state when unconstrained. As described below, the expandable stent graft 130 may be configured to couple to an arteriovenous graft of a patient such that the arteriovenous graft is in fluid communication with the second tubular conduit 120.

In some embodiments, one or both of the inner surface and the outer surface of the vascular access assembly 100 may be associated with a therapeutic agent. In other words, the therapeutic agent may be disposed on or embedded within a surface of the vascular access assembly 100. The therapeutic agent may be released from the surface(s) of the vascular access assembly 100 to deliver a therapeutically effective dose of the therapeutic agent to the patient when the vascular access assembly 100 is implanted within a patient. In some embodiments, a first therapeutic agent is associated with the inner surface of the vascular access assembly 100 and a second therapeutic agent that differs from the first therapeutic agent is associated with the outer surface of the vascular access assembly 100. In such embodiments, both the first therapeutic agent and the second therapeutic agent may be delivered into the bloodstream of the patient in therapeutically effective doses when the vascular access assembly 100 is implanted within the patient. In some embodiments, heparin is used as a therapeutic agent. In some embodiments, the therapeutic agent reduces thrombus or tissue proliferation.

In some embodiments, the vascular access assembly 100 further includes one or more connectors 122 that facilitate coupling of the first tubular conduit 110 to the second tubular conduit 120. In some embodiments, such as the embodiment shown in FIGS. 1 and 2, the connector 122 is disposed at a central end the second tubular conduit 120.

In the depicted embodiment, the connector 122 includes one or more barbs or protrusions 124 that are designed to engage with an inner diameter of the first tubular conduit 110 to form a fluid-tight connection. While FIGS. 1 and 2 show the connector 122 at the central end of the second tubular conduit 120, a skilled artisan will recognize that, in other embodiments, the connector 122 may instead be disposed at a peripheral end of the first tubular conduit 110. In still other embodiments, the connector 122 may include components disposed at both the central end of the second tubular conduit 120 and the peripheral end of the first tubular conduit 110. The connector 122 may be made from any suitable material, such as steel or titanium.

The vascular access assembly 100 may be used in any suitable medical procedure, such as to establish vascular access for hemodialysis. For example, where an arteriovenous graft has become occluded or otherwise failed, an alternative artificial flow path that bypasses the occlusion or failure may be established. For example, an artificial flow path may be established from a portion of the arteriovenous graft that is upstream of the occlusion or failure in the arteriovenous graft to the right atrium of the heart.

Figure 3:
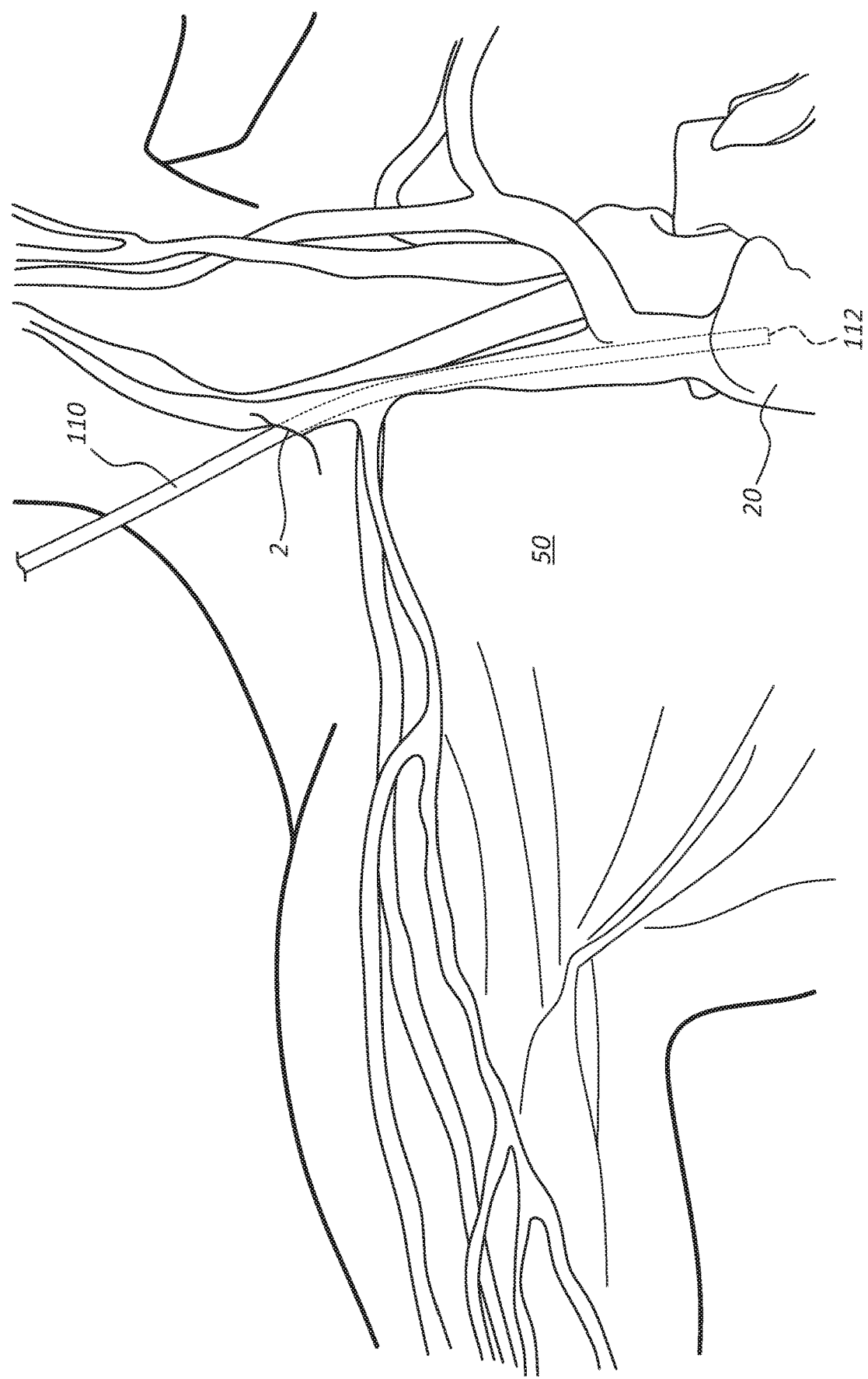
FIG. 3 depicts a first tubular conduit of the vascular access assembly of FIGS. 1 and 2 that has been inserted into a patient such that a central end of the first tubular conduit is disposed within a right atrium of a patient.

As shown in FIG. 3, such a medical procedure may initially involve making a first incision 2 in or adjacent to the neck of a patient 50 to access the internal jugular vein of the patient 50. A guidewire may then be passed into the internal jugular vein to the inferior vena cava, followed by a dilator that is passed over the guidewire to facilitate insertion of an introducer. The dilator may then be removed, and the introducer passed over the guidewire into the internal jugular vein of the patient 50. Once the introducer is placed within the internal jugular vein, a central end 112 of the first tubular conduit 110 may be inserted through the introducer and advanced within the patient 50 such that the central end 112 of the first tubular conduit 110 passes through the superior vena cava into the right atrium of a heart 20 as depicted in FIG. 3. Advancement of the first tubular conduit 110 into the patient 50 may be done under fluoroscopic guidance.

Figure 4:
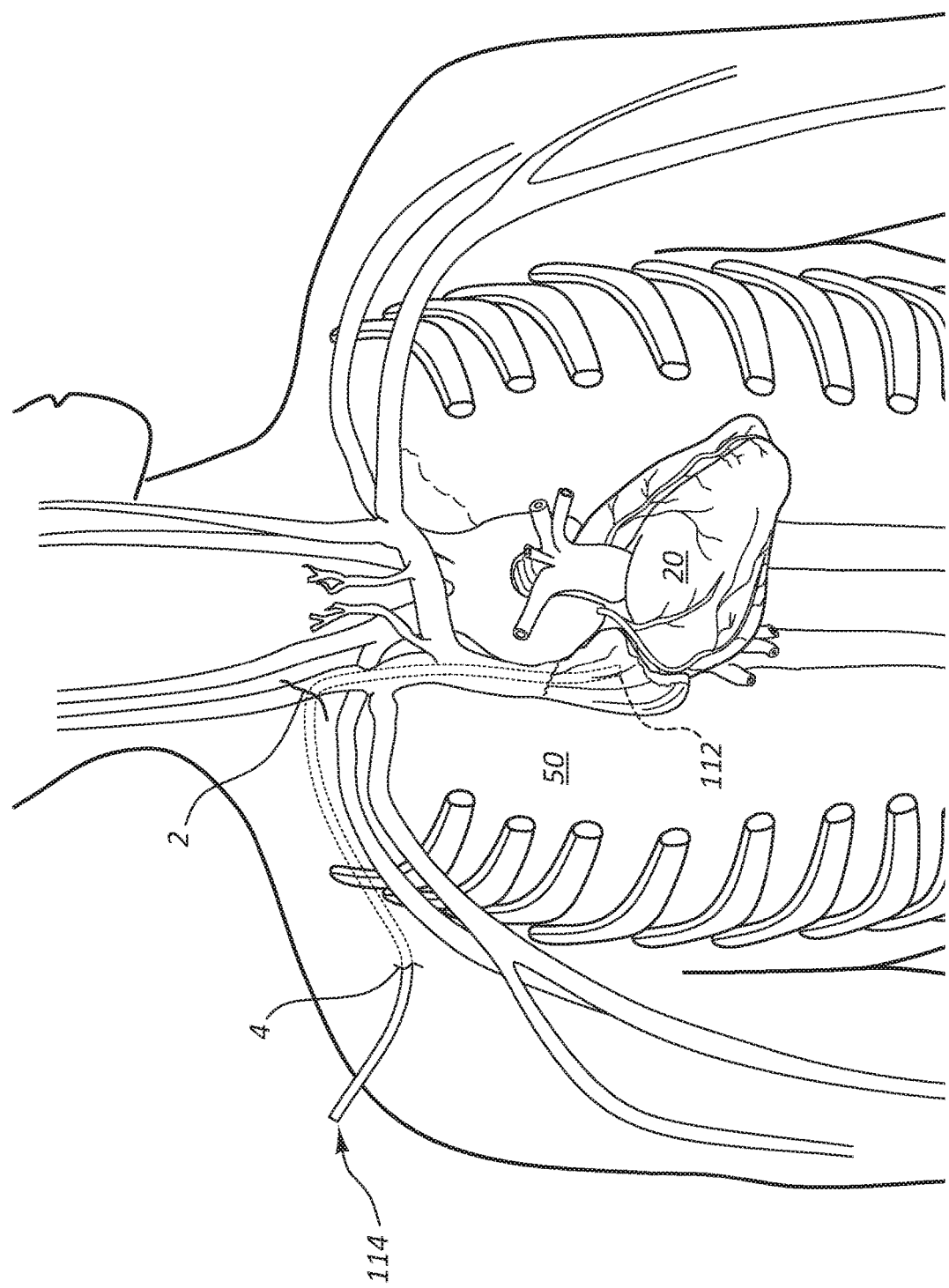
FIG. 4 depicts the first tubular conduit of the vascular access assembly of FIGS. 1 and 2 that has been placed into a patient such that a peripheral end of the first tubular conduit is disposed adjacent an incision in the shoulder region of the patient.

After the central end 112 of the first tubular conduit 110 has been placed within the right atrium of the heart 20, a second incision 4 (see FIG. 4) may be made in the shoulder region of the patient 50 (e.g., adjacent the deltopectoral groove). A tunneling device may then be used to establish a subcutaneous path between the first incision 2 in the neck region of the patient 50 and the second incision 4 in the shoulder region of the patient 50. The peripheral end 114 of the first tubular conduit 110 may then be inserted into the first incision 2 and advanced along the path established by the tunneling device (i.e., the first tubular conduit 110 is tunneled) such that the first tubular conduit 110 extends from the right atrium of the heart 20 to the second incision 4 in the shoulder region of the patient 50 as shown in FIG. 4.

Once the first tubular conduit 110 has been placed such that the first tubular conduit 110 extends from the right atrium of the heart 20 to the second incision 4 in the shoulder region of the patient 50, a third incision 6 (see FIG. 5) may be made in the arm of the patient 50 adjacent the target site of an arteriovenous graft 70. For example, the third incision 6 may be made at a position that is upstream of an occlusion or failure in the arteriovenous graft 70. The expandable stent graft 130 at the peripheral end of the second tubular conduit 120 may then be coupled to the arteriovenous graft 70 adjacent the third incision 6 in the arm of the patient 50 (see FIGS. 5 and 6). For example, in some embodiments, the arteriovenous graft 70 may be pierced adjacent the third incision 6 by a needle. A guidewire may then be inserted through the needle and into the arteriovenous graft 70 of the patient 50. In some embodiments, a distal end of a stent graft deployment device (not shown) may then be passed over the guidewire and inserted into the arteriovenous graft 70 of the patient 50. The practitioner may then manipulate the stent graft deployment device and expandable stent graft 130 to deploy the expandable stent graft 130 in the arteriovenous graft 70 of the patient 50. For example, a sheath of the stent graft deployment device may be retracted, thereby allowing a self-expanding stent to deploy within the arteriovenous graft 70 of the patient 50. In some such embodiments, the second tubular conduit 120 may be disposed within a deployment device such that the expandable stent graft 130 is disposed distal (along the deployment device) from the remaining portion of the second tubular conduit 120, allowing the expandable stent graft 130 to be advanced by the deployment device into a bodily structure before the remaining portion of the second tubular conduit 120. In other embodiments, a pull string 132 (see FIGS. 1 and 2) is used to deploy the expandable stent graft 130 within the arteriovenous graft 70 of the patient 50. In still other embodiments, the expandable stent graft 130 is deployed via a balloon catheter.

Figure 5:
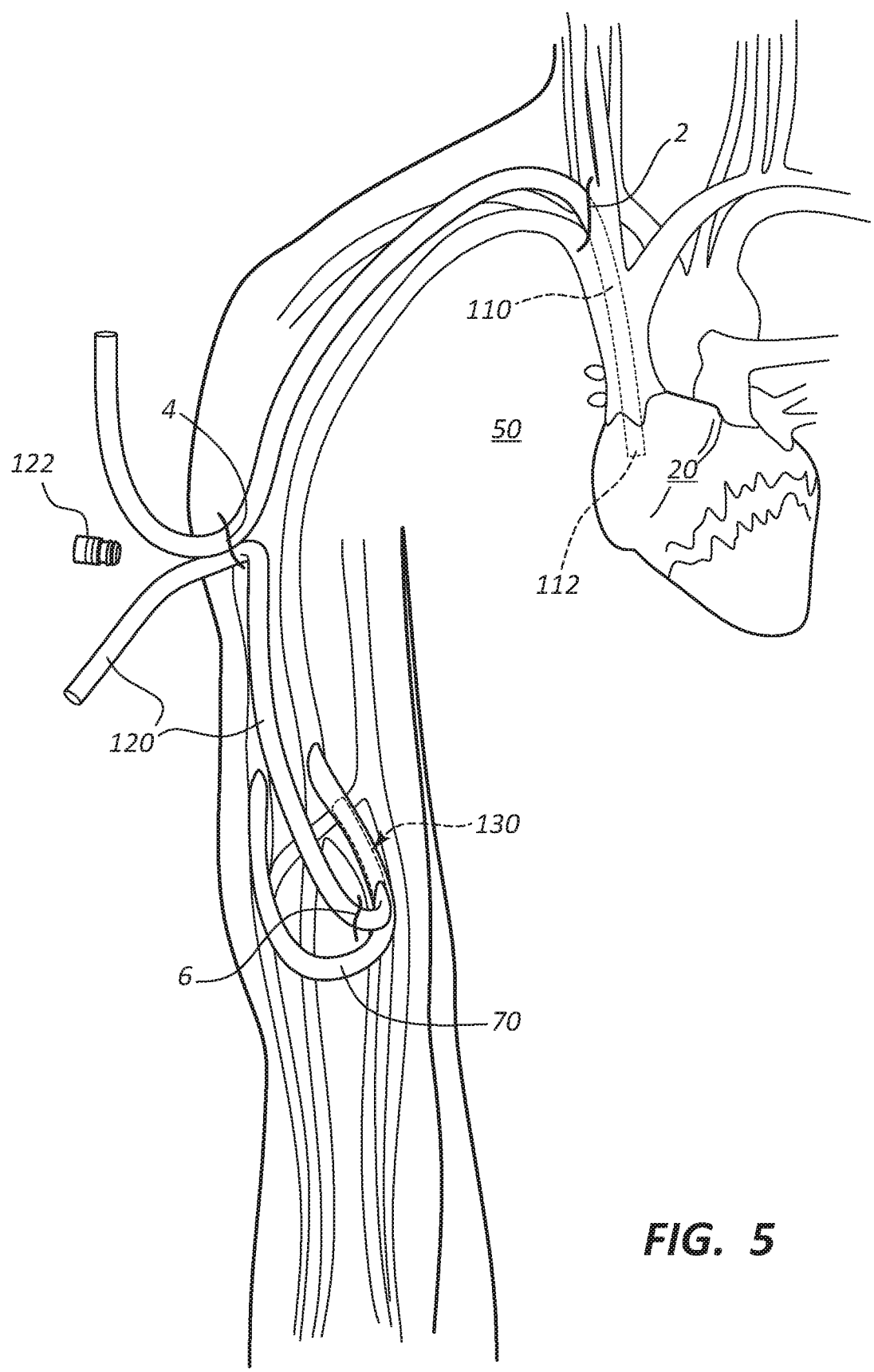
FIG. 5 depicts a second tubular conduit of the vascular access assembly of FIGS. 1 and 2 that has been inserted into a patient such that the second tubular conduit extends from an incision adjacent arteriovenous graft to the incision in the shoulder region of the patient.
Figure 6:
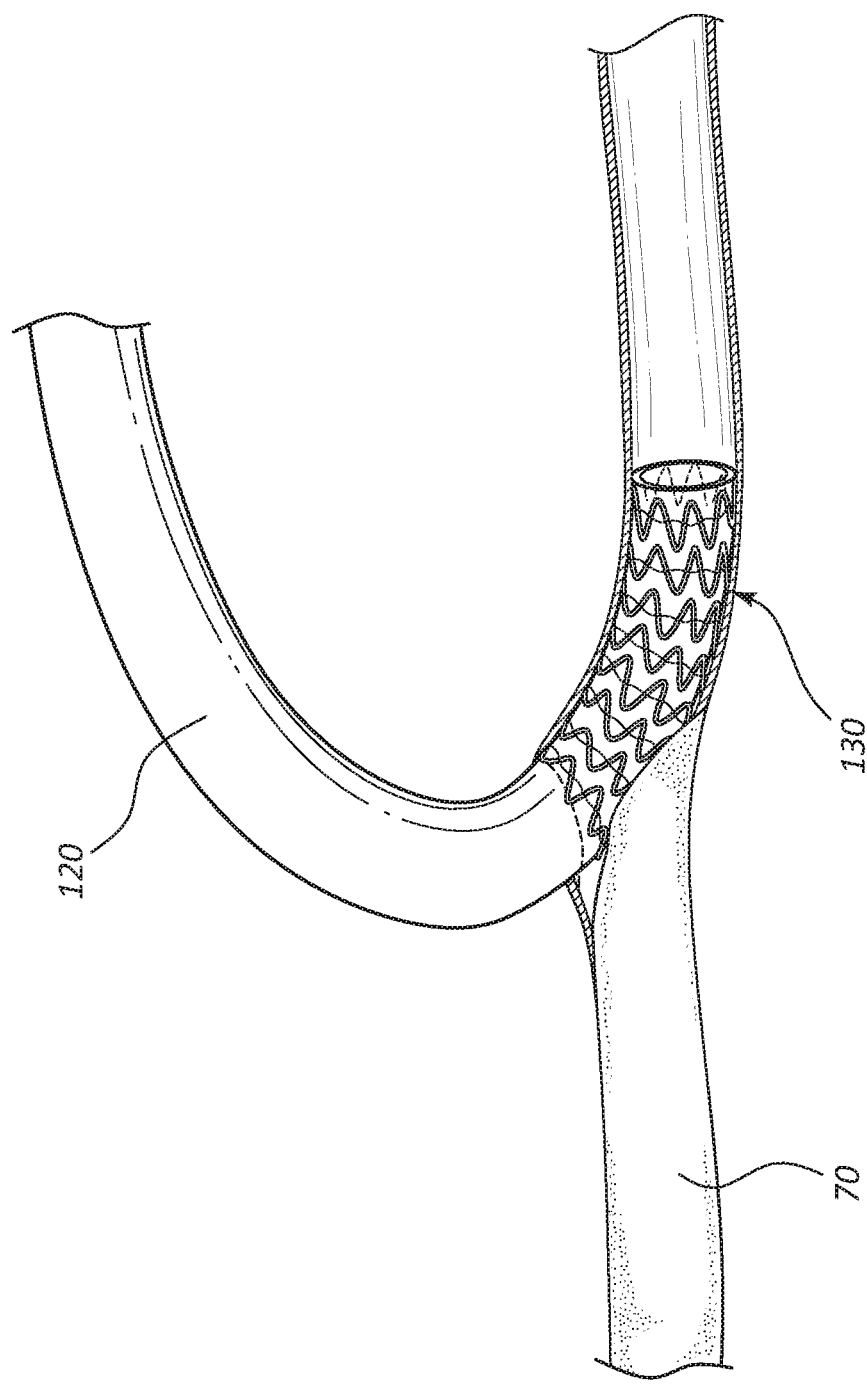
FIG. 6 provides a close-up perspective view of a portion of the vascular access assembly of FIGS. 1 and 2 with the stent graft deployed in an arteriovenous graft.

In other words, the expandable stent graft 130 may be inserted into the arteriovenous graft 70 when in a compact state. Once the expandable stent graft 130 is appropriately positioned within the arteriovenous graft 70, the expandable stent graft 130 may be deployed, thereby forming a fluid-tight seal with the arteriovenous graft 70 as shown in FIGS. 5 and 6. The fluid-tight seal formed by deployment of the expandable stent graft 130 may divert essentially all of the blood from the arteriovenous graft 70 into the second tubular conduit 120 of the vascular access assembly 100.

A tunneling device may then be used to establish a subcutaneous path between the third incision 6 in the arm of the patient 50 to the second incision 4 in the shoulder region of the patient 50 (see FIG. 5). The second tubular conduit 120 may then be inserted into and advanced through the tunneling device such that the second tubular conduit 120 extends from the third incision 6 to the second incision 4. The tunneling device may then be removed such that the second tubular conduit 120 is disposed within the patient 50 as shown in FIG. 5. In this manner, the tunneling device may facilitate placement and delivery of the second tubular conduit 120 within the patient 50.

With the central end 112 of the first tubular conduit 110 disposed within the right atrium of the heart 20 of the patient 50, the peripheral end of the first tubular conduit 110 may then, if needed, be cut to the appropriate length. In other words, the first tubular conduit 110 may initially (e.g., when manufactured and inserted as described above) have a length that is longer than is needed to establish a flow path from the right atrium of the heart 20 of the patient 50 to the second incision 4 in the shoulder region of the patient 50. The first tubular conduit 100 may then be cut to proper length to facilitate coupling of the second tubular conduit 120 to the first tubular conduit 110 at the second incision 4 in the shoulder region of the patient 50.

Similarly, in some embodiments, the second tubular conduit 120 has an initial length that is longer than is needed to establish a flow path from the second incision 4 in the shoulder region of the patient 50 to the third incision 6 in the arm of the patient 50. In such embodiments, the central end of the second tubular conduit 120 may be cut to the appropriate length once the second tubular conduit 120 has been inserted into the patient 50. In some embodiments, the connector 122 (see FIG. 5) may then be attached to the newly formed central end of the second tubular conduit 120. In other embodiments, no cutting of the second tubular conduit 120 is needed.

Figure 7:
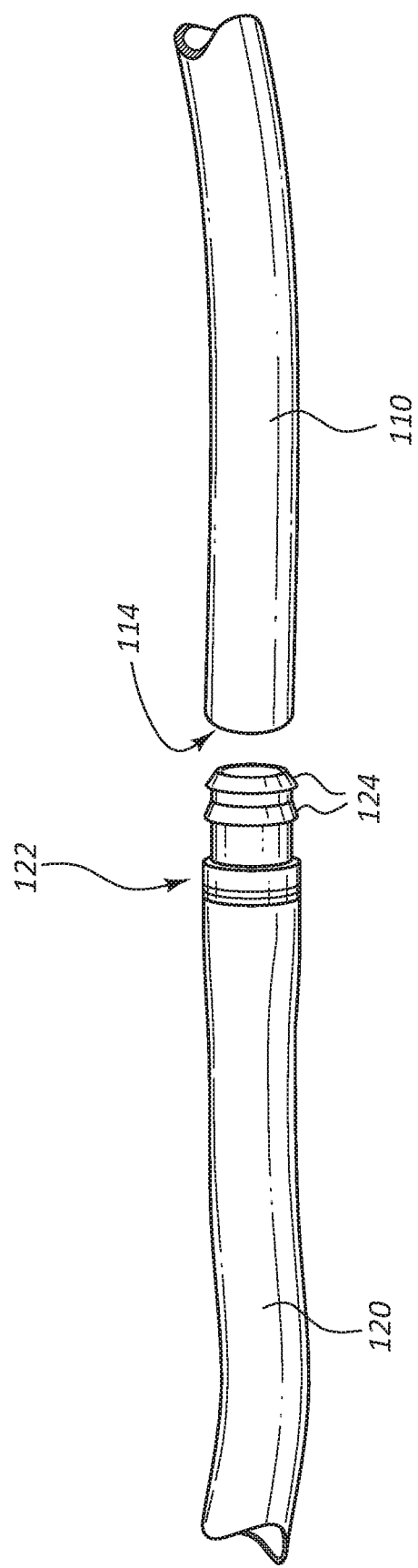
FIG. 7 depicts a coupling mechanism of the vascular access assembly of FIGS. 1 and 2 for coupling of the first tubular conduit to the second tubular conduit.

Once the first tubular conduit 110 and the second tubular conduit 120 are the proper length, the second tubular conduit 120 may be coupled to the first tubular conduit 110. For example, the connector 122 at the central end of the second tubular conduit 120 may be inserted to the peripheral end 114 of the first tubular conduit 110 such that the barbs or protrusions 124 of the connector 122 engage with an inner diameter of the first tubular conduit 110 (see FIG. 7). Such engagement may establish a fluid-tight connection between the first tubular conduit 110 and the second tubular conduit 120. Establishment of a fluid-tight connection can be confirmed by attaching the peripheral end of the second tubular conduit 120 to a syringe and advancing fluid (e.g., heparinized saline) through the system.

Figure 8:
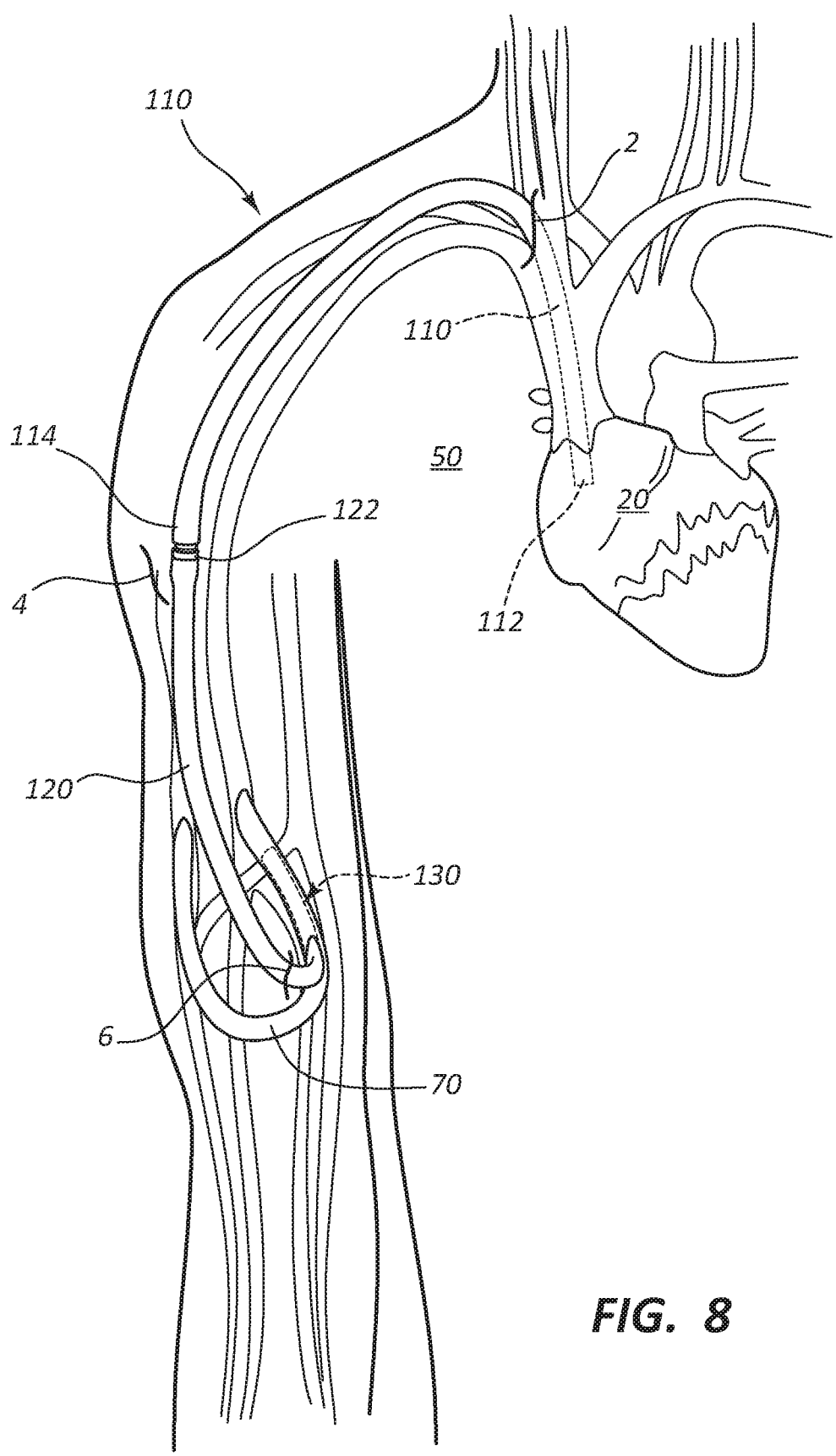
FIG. 8 depicts the vascular access assembly of FIGS. 1 and 2 in a fully implanted configuration.

Once a flow path from the arteriovenous graft 70 to the heart 20 has been established as shown in FIG. 8, the first incision 2, the second incision 4, and the third incision 6 may be closed via any suitable technique. In this manner, the vascular access assembly 100 may, when implanted and assembled, be a fully subcutaneous surgical implant. The implanted and assembled vascular access assembly 100 may also, as described above, be implanted without establishing a venous anastomosis.

The implanted vascular access assembly 100 may be used to facilitate vascular access. For example, in the case of hemodialysis, a practitioner may insert a first needle through the skin of the patient 50 and into the vascular access assembly 100. More particularly, the first needle may be inserted into the second tubular conduit 120. Fluid may be withdrawn from the vascular access assembly 100 and drawn into a dialysis machine that purifies the blood. The purified blood may then be returned to the patient 50 via a second needle that extends through the skin of the patient 50 and into more central location of the second tubular conduit 120.

The steps of the procedure described above are only exemplary in nature. In other words, the vascular access assembly 100 may be implanted into the patient 50 via a procedure that deviates somewhat from the procedure described above. One of ordinary skill in the art, having the benefit of this disclosure, will also appreciate that some of the steps described above need not be performed in the precise order that is specified above.

FIGS. 9 and 10 depict an embodiment of a vascular access assembly 200 that resembles the vascular access assembly 100 described above in certain respects. Accordingly, like features are designated with like reference numerals, with the leading digits incremented to "2." For example, the embodiment depicted in FIGS. 9 and 10 includes a first tubular conduit 210 that may, in some respects, resemble the first tubular conduit 110 of FIGS. 1-8. Relevant disclosure set forth above regarding similarly identified features thus may not be repeated hereafter. Moreover, specific features of the vascular access assembly 100 and related components shown in FIGS. 1-8 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access assembly 200 and related components depicted in FIGS. 9 and 10. Any suitable combination of the features, and variations of the same, described with respect to the vascular access assembly 100 and related components illustrated in FIGS. 1-8 can be employed with the vascular access assembly 200 and related components of FIGS. 9 and 10, and vice versa. This pattern of disclosure applies equally to further embodiments depicted in subsequent figures and described hereafter, wherein the leading digits may be further incremented.

FIG. 9 depicts the implanted vascular access assembly 200 with an expandable stent graft 230 that, in contrast to the embodiment depicted in FIGS. 1-8, is branched. A close-up view of a portion of the vascular access assembly 200 is depicted in FIG. 10. The branched expandable stent graft 230 of the vascular access assembly 200 may be used to couple to an artery 80 of the patient 50. In other words, the vascular access assembly 200 may be configured for coupling to an artery 80 of the patient 50 instead of coupling to an arteriovenous graft as described above in connection with FIGS. 1-8.

The vascular access assembly 200 may be implanted within the patient 50 in a manner analogous to the procedure described above in connection with the vascular access assembly 100. However, instead of inserting the expandable stent graft 230 at the peripheral end of a second tubular conduit 220 into an arteriovenous graft, the expandable stent graft 230 may be inserted into and deployed in an artery 80 (e.g., a brachial artery) such that a first branch of the expandable stent graft 230 permits fluid flow through the artery 80 and a second branch is configured to direct blood from the artery 80 to the right atrium of the heart 20 of the patient 50. In this manner, an artificial fully subcutaneous flow path may be established from an artery 80 to the heart 20 of the patient 50.

In the depicted embodiment, the branched expandable stent graft 230 is T-shaped. However, in other embodiments, the branched stent graft may be some other branched shape (e.g., Y-shaped). The portions of the expandable stent graft 230 configured for displacement within the artery may be sized such that an outside diameter of the expandable stent graft 230 contacts the inside diameter of the artery wall, in some instances sealing against the wall to prevent blood flow around the outside diameter of the expandable stent graft 230.

Figure 11:
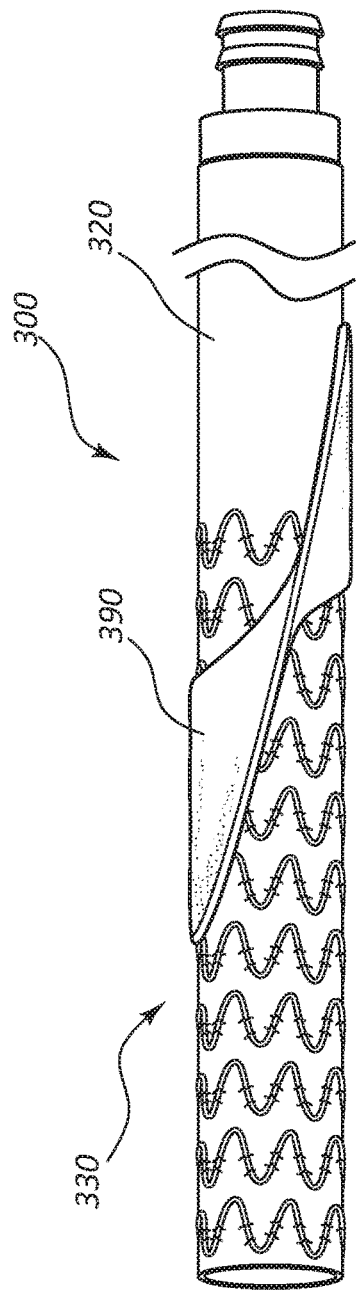
FIG. 11 provides a side view of a portion of a vascular access assembly according to another embodiment in which a collar is disposed around a periphery of the expandable stent graft in a collapsed configuration.
Figure 12:
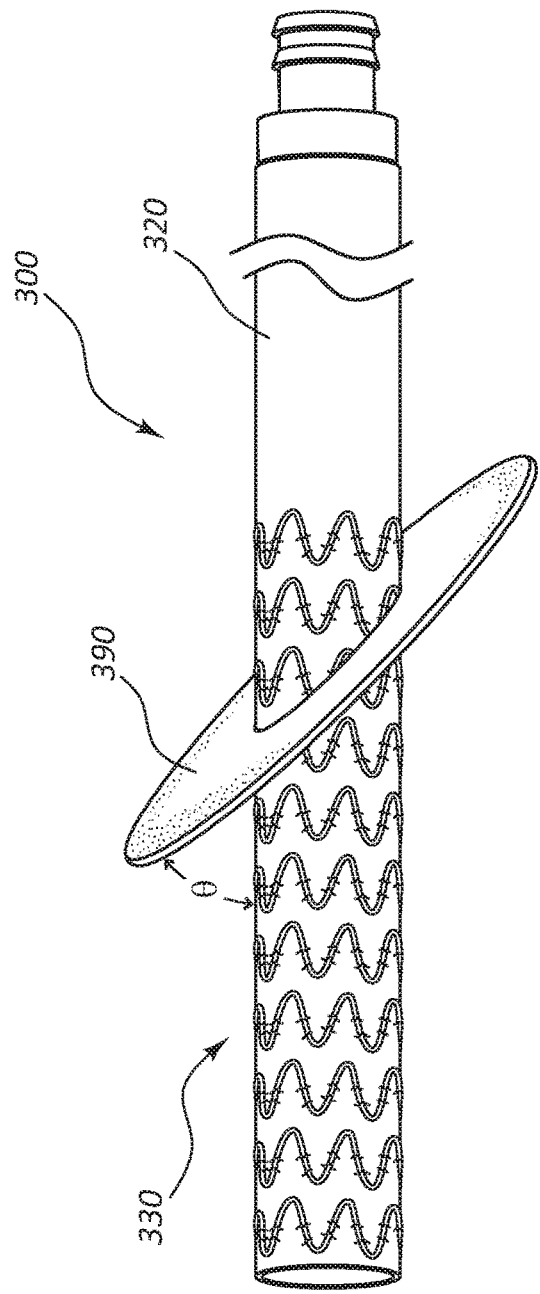
FIG. 12 provides a side view of the portion of the vascular access assembly of FIG. 11, with the collar in an uncollapsed configuration.
Figure 13:
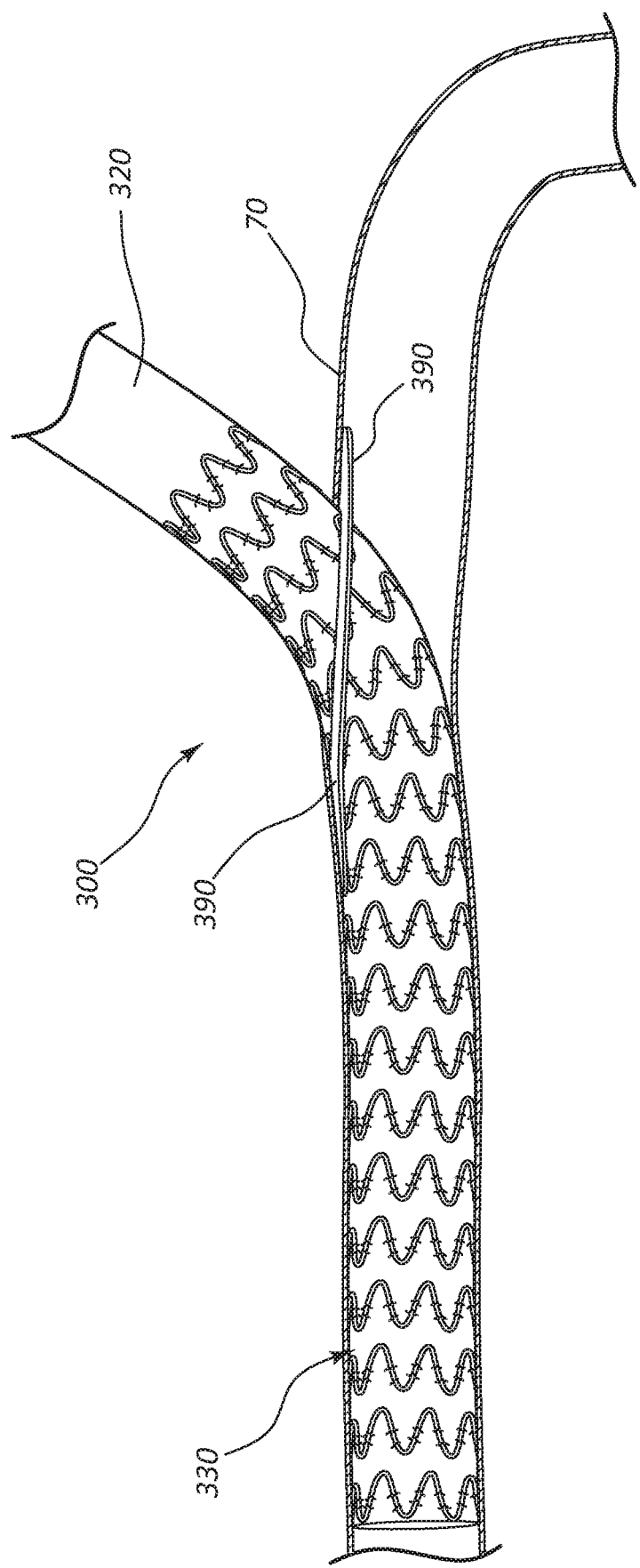
FIG. 13 provides a cross-sectional side view of the portion of the vascular access assembly of FIGS. 11 and 12 in an artery of a patient.

FIGS. 11-13 are alternative views of a portion of a vascular access assembly 300 according to another embodiment. More particularly, FIGS. 11 and 12 depict a second tubular conduit 320 and an expandable stent graft 330 that is coupled to the peripheral end of the second tubular conduit 320. In the depicted embodiment, the vascular access assembly 300 includes a collar 390 that is disposed around a periphery of the expandable stent graft 330.

In some embodiments, the collar 390 is configured to transition between a compact state (FIG. 11) in which the collar 390 adopts a low-profile configuration to a deployed state (FIGS. 12 and 13) in which the collar 390 extends outward from the exterior surface of the expandable stent graft 330. When the expandable stent graft 330 is initially inserted into the arteriovenous graft 70 or an artery of the patient 50, the collar 390 may be in a compact state as shown in FIG. 11. Once the expandable stent graft 330 has been inserted into the arteriovenous graft 70 or the artery of the patient 50, the collar 390 may transition to the deployed state as shown in FIG. 12. In some embodiments, this transition occurs as the expandable stent graft 330 is deployed. In some instances, the collar 390 may be deployed before the entire expandable stent graft 330 to facilitate positioning of the expandable stent graft 330. For example, an expanded collar 390 may be brought into contact with a wall of the arteriovenous graft 70 or an artery of the patient 50, before the entire expandable stent graft 330 is expanded and is thus more easily displaceable. The collar 390 may be any suitable shape. For example, in the depicted embodiment, the collar 390 is a relatively thin, ring-shaped sheet of material.

In some embodiments, the collar 390, when unconstrained, is angled relative to the expandable stent graft 330. For example, the collar 390 may form an acute angle (θ) with the expandable stent graft 330. In some embodiments, the acute angle θ is between 15° and 75°, between 30° and 60°, and/or between 35° and 55°. The angle relationship between the collar 390 and the expandable stent graft 330 may facilitate positioning of the collar 390 to function as a seal. For example, as shown in FIG. 13, the deployed collar 390 may function as a seal, thereby preventing or reducing the leakage of blood from the opening in the arteriovenous graft 70 or artery into which the expandable stent graft 330 has been inserted. The collar 390 may also prevent or reduce the risk of withdrawal of the expandable stent graft 330 from the arteriovenous graft 70 or the artery. Stated differently, the collar 390 may serve as a stop that prevents withdrawal of the expandable stent graft 330 from the arteriovenous graft 70 or the artery.

During placement and/or implantation of vascular access assemblies, such as those describe above, various strategies may be employed to reduce or prevent the loss of blood. For example, in some embodiments, various clamps are used during implantation to restrict fluid flow through a portion of the first tubular conduit and/or the second tubular conduit. In other or further embodiments, the first tubular conduit and/or the second tubular conduit include one of more valves that obstruct fluid flow, thereby preventing the loss of blood during implantation. For example, in some embodiments, a valve is disposed adjacent the peripheral end of the first tubular conduit or the central end of the second tubular conduit. The valve may be configured to transition from a first configuration that prevents fluid flow through the valve when the first tubular conduit and the second tubular conduit are uncoupled from each other to a second configuration that allows fluid flow through the valve when the first tubular conduit and the second tubular conduit are coupled to each other. In some embodiments, fluid flow is restricted by a balloon that is disposed within a portion of the vascular access assembly.

Kits that include a vascular access assembly are also within the scope of this disclosure. For example, a kit may include any of the vascular access assemblies described above. The kit may also include other elements, such as instructions for using the vascular access assembly to establish a flow path from an artery or an arteriovenous graft of a patient to a heart of the patient. Kits may additionally or alternatively include (1) one or more clamps for preventing fluid flow through a portion of a tubular conduit, (2) scissors, (3) plugs for preventing fluid flow through an end of a tubular conduit, (4) a tunneling device, (5) a syringe, (6) one or more guidewires, (7) gauze pads, (8) contrast fluid, and/or (9) saline (e.g., heparinized saline), among other potential elements.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A vascular access assembly comprising:
   a first tubular conduit;
   a second tubular conduit;
   an expandable stent graft that is coupled to the second tubular conduit adjacent a peripheral end of the second tubular conduit, wherein the expandable stent graft includes a first branch configured to couple to an artery, vein or arteriovenous graft of a patient such that the first branch permits blood flow through the artery, vein, or arteriovenous graft, wherein the expandable stent graft includes a second branch coupled to the second tubular conduit such that the artery, the vein, or the arteriovenous graft is in fluid communication with the second tubular conduit;
   a restraint comprising a pull string coupled to filaments surrounding the expandable stent graft in a compressed state;

wherein the first tubular conduit is configured to couple to a central end of the second tubular conduit to form a flow path that extends from the artery, the vein, or the arteriovenous graft to a heart of the patient.

2. The vascular access assembly of claim 1, wherein the expandable stent graft comprises a T-shape.

3. The vascular access assembly of claim 1, wherein the second tubular conduit comprises a puncturable and self-sealing wall such that the wall may be punctured by insertion of a needle and then reseal upon withdrawal of the needle.

4. The vascular access assembly of claim 1, further comprising a connector for coupling the first tubular conduit to the second tubular conduit.

5. The vascular access assembly of claim 1, wherein the second tubular conduit is configured for delivery through a lumen of a deployment device.

6. The vascular access assembly of claim 1, wherein the flow path extends from the brachial artery to a right atrium of the heart.

7. The vascular access assembly of claim 1, wherein the vascular access assembly is configured to be implanted without establishing a venous anastomosis.

8. The vascular access assembly of claim 1, further comprising a valve disposed adjacent a central end of the second tubular conduit, wherein the valve is configured to allow blood flow across the valve when the second tubular conduit is coupled to the first tubular conduit and to prevent blood flow across the valve when the second tubular conduit is uncoupled from the first tubular conduit.

9. The vascular access assembly of claim 1, wherein the expandable stent graft is a self-expanding stent graft.

10. The vascular assembly of claim 1, further comprising a tubular liner that is disposed within both the expandable stent graft and the second tubular conduit, wherein the tubular liner provides a continuous luminal surface for contact with blood of the patient.

11. The vascular assembly of claim 1, further comprising a first therapeutic agent that is associated with one or both of an inner surface and an outer surface of the vascular access assembly, wherein the vascular access assembly is configured to deliver a therapeutically effective dose of the first therapeutic agent to the patient when the vascular access assembly is implanted within the patient.

12. A method for implanting a vascular access assembly into a patient, the method comprising:

inserting a central end of a first tubular conduit into a patient such that the central end of the first tubular conduit is positioned within a right atrium of a heart of the patient;

tunneling a peripheral end of the first tubular conduit through flesh of the patient to an incision adjacent a shoulder of the patient;

inserting a second tubular conduit into the patient such that the second tubular conduit extends from the incision adjacent the shoulder of the patient to an incision in the arm of the patient;

deploying a stent graft within an artery or an arteriovenous graft in the arm of the patient, wherein the stent graft is coupled to and disposed adjacent a peripheral end of the second tubular conduit;

pulling a pull string to remove a restraint from around the stent graft, wherein the stent graft transitions from a compressed state to an expanded state;

sealing an insertion site of the artery or the arteriovenous graft with a collar disposed around a periphery of the stent graft; and coupling the first tubular conduit to the second tubular conduit.

13. The method of claim 12, wherein the stent graft is deployed in the brachial artery.

14. The method of claim 12, wherein the stent graft is deployed in the artery of the patient and the stent graft is a branched stent graft.

15. The method of claim 12, wherein implantation of the vascular access assembly does not involve venous anastomosis.

16. The method of claim 12, wherein the stent graft is deployed in an arteriovenous graft and the stent graft is an unbranched stent graft.

17. The method of claim 16, wherein the stent graft, when deployed, forms a fluid-tight seal that diverts the blood from the arteriovenous graft to a flow path that extends to the heart of the patient.

18. The method of claim 12, wherein deploying the stent graft comprises inflating a balloon to expand to the stent graft.

19. The method of claim 18, wherein the peripheral end of the second tubular conduit is tunneled through the flesh by passing the peripheral end of the second tubular conduit through a deployment device.

20. The method of claim 12, wherein the pull string is coupled to filaments surrounding the stent graft in the compressed state.

\* \* \* \* \*